(12) United States Patent
Andreiko et al.

(10) Patent No.: US 11,363,938 B2
(45) Date of Patent: Jun. 21, 2022

(54) FEEDBACK CONTROL MECHANISM FOR ADJUSTMENT OF IMAGING PARAMETERS IN A DENTAL IMAGING SYSTEM

(71) Applicant: Ormco Corporation, Orange, CA (US)

(72) Inventors: Craig A. Andreiko; Robert F. Dillon, Bedford, NH (US); Andrew F. Vesper, Townsend, MA (US)

(73) Assignee: Ormco Corporation, Orange, CA (US)

( * ) Notice: Subject to any disclaimer, the term of this patent is extended or adjusted under 35 U.S.C. 154(b) by 1417 days.

(21) Appl. No.: 14/209,487

(22) Filed: Mar. 13, 2014

(65) Prior Publication Data
US 2014/0272765 A1    Sep. 18, 2014

Related U.S. Application Data

(60) Provisional application No. 61/784,441, filed on Mar. 14, 2013.

(51) Int. Cl.
    *A61B 1/00* (2006.01)
    *A61B 1/253* (2006.01)
    *A61C 9/00* (2006.01)

(52) U.S. Cl.
    CPC ...... *A61B 1/00006* (2013.01); *A61B 1/00009* (2013.01); *A61B 1/253* (2013.01); *A61C 9/0053* (2013.01)

(58) Field of Classification Search
    None
    See application file for complete search history.

(56) References Cited

U.S. PATENT DOCUMENTS

| | | | |
|---|---|---|---|
| 4,202,014 A * | 5/1980 | Gilligan | H04N 5/2353 348/362 |
| 5,519,437 A * | 5/1996 | Nelvig | H04N 5/32 348/162 |
| 5,664,001 A * | 9/1997 | Tachibana | A61B 6/14 378/108 |
| 5,677,940 A * | 10/1997 | Suzuki | H04N 5/32 250/370.09 |
| 5,741,132 A * | 4/1998 | Usui | A61B 1/253 433/30 |
| 6,404,854 B1 * | 6/2002 | Carroll | A61B 6/145 348/E3.02 |
| 6,597,934 B1 * | 7/2003 | de Jong | G06T 1/0007 600/407 |
| 6,617,559 B1 * | 9/2003 | Emery | G01J 1/4204 250/205 |
| 7,016,461 B2 * | 3/2006 | Rotondo | A61B 6/14 378/39 |
| 7,068,825 B2 * | 6/2006 | Rubbert | A61C 7/00 382/128 |
| 7,099,056 B1 * | 8/2006 | Kindt | H04N 5/2351 348/96 |
| 8,675,290 B2 * | 3/2014 | Rohaly | G03B 35/08 359/618 |
| 9,451,873 B1 * | 9/2016 | Kopelman | A61B 1/00009 |

(Continued)

*Primary Examiner* — Samah A Beg
(74) *Attorney, Agent, or Firm* — Wood Herron & Evans LLP

(57) ABSTRACT

Provided are a system, method, and computer readable storage medium in which data is received from a dental imaging system. The received data is analyzed to adjust one or more imaging parameters of the dental imaging system.

22 Claims, 15 Drawing Sheets

(56) References Cited

U.S. PATENT DOCUMENTS

| | | | | |
|---|---|---|---|---|
| 2001/0055368 A1* | 12/2001 | Carroll | | A61B 6/14 378/189 |
| 2002/0015934 A1* | 2/2002 | Rubbert | | A61C 7/00 433/29 |
| 2002/0085673 A1* | 7/2002 | Rinaldi | | A61B 6/14 378/108 |
| 2004/0252303 A1* | 12/2004 | Giorgianni | | G01J 3/50 356/402 |
| 2005/0242269 A1* | 11/2005 | Hayashi | | A61B 6/14 250/208.1 |
| 2008/0170124 A1* | 7/2008 | Hatanaka | | G06T 5/004 348/208.4 |
| 2009/0040364 A1* | 2/2009 | Rubner | | G06T 3/4053 348/362 |
| 2009/0232274 A1* | 9/2009 | Spartiotis | | A61B 6/14 378/39 |
| 2010/0268069 A1* | 10/2010 | Liang | | G06T 7/521 600/425 |
| 2011/0274332 A1* | 11/2011 | Crucs | | A61B 6/14 382/132 |
| 2012/0013723 A1* | 1/2012 | Laxhuber | | A61C 19/00 348/77 |
| 2012/0062557 A1* | 3/2012 | Dillon | | A61C 7/002 345/419 |
| 2012/0092461 A1* | 4/2012 | Fisker | | A61B 5/0068 348/46 |
| 2012/0177352 A1* | 7/2012 | Pillman | | H04N 5/23248 396/61 |
| 2012/0327192 A1* | 12/2012 | Pfeiffer | | A61B 5/1077 348/46 |
| 2013/0330684 A1* | 12/2013 | Dillon | | A61B 1/00039 433/29 |
| 2014/0022352 A1* | 1/2014 | Fisker | | G06T 5/003 348/46 |
| 2014/0335469 A1* | 11/2014 | Boyden | | A61B 5/4803 433/27 |
| 2015/0017598 A1* | 1/2015 | Wu | | A61C 9/006 433/29 |
| 2016/0262715 A1* | 9/2016 | Charnegie | | A61B 6/545 |
| 2016/0330374 A1* | 11/2016 | Ilic | | H04N 5/23251 |
| 2017/0224272 A1* | 8/2017 | Liu | | A61B 5/0088 |

\* cited by examiner

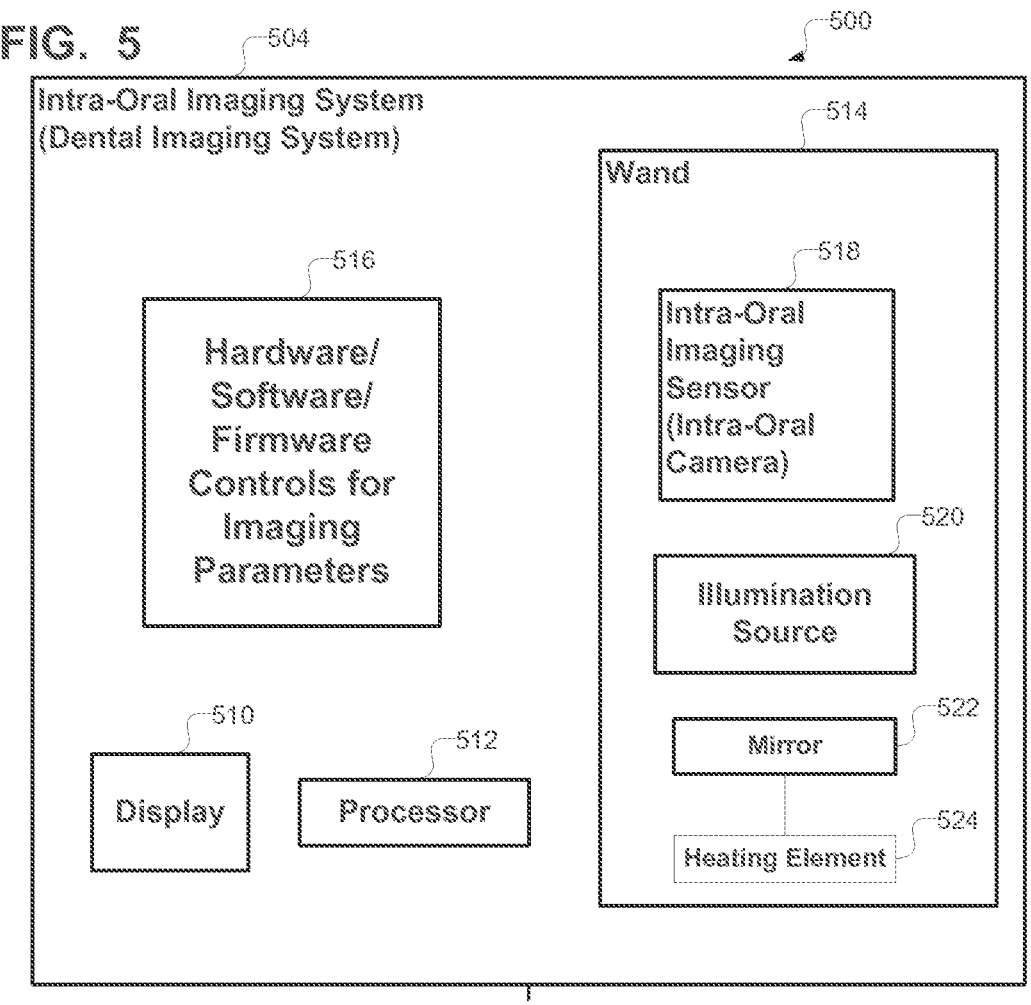
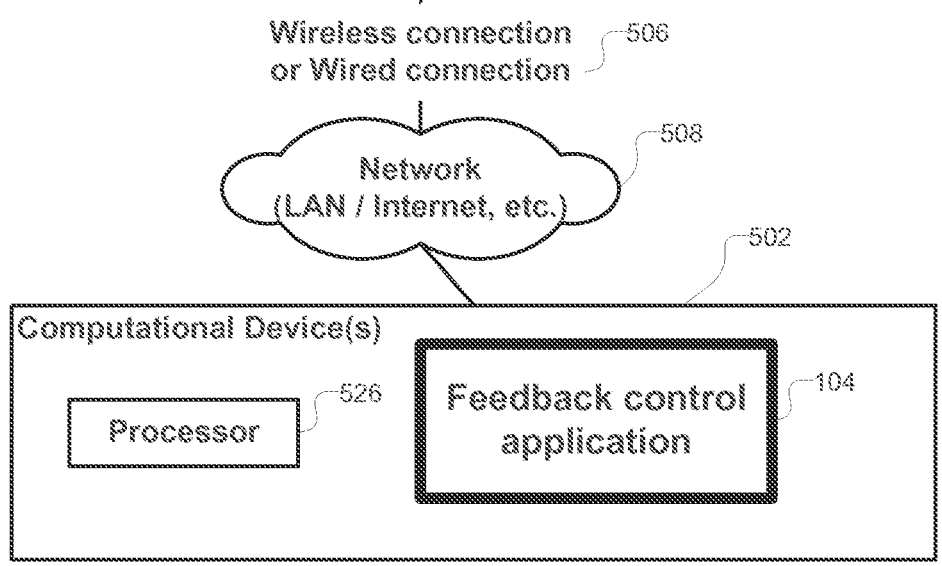
FIG. 5 ived data.

FEEDBACK CONTROL MECHANISM FOR ADJUSTMENT OF IMAGING PARAMETERS IN A DENTAL IMAGING SYSTEM

CROSS-REFERENCE TO RELATED APPLICATION

This application claims the benefit of U.S. Provisional Application No. 61/784,441, filed Mar. 14, 2013, which Provisional Application is incorporated by reference in its entirety.

FIELD

The disclosure relaxes to a method, system, and computer readable storage medium for a feedback control mechanism for the adjustment of imaging parameters in a dental imaging system.

BACKGROUND

An intra-oral imaging system is a diagnostic equipment that allows a dental practitioner to see the inside of a patient's month and display the topographical characteristics of teeth on a display unit. Certain three-dimensional (3D) intra-oral imagers may be comprised of an intra-oral camera with a light source. The 3D intra-oral imager may be inserted into the oral cavity of a patient by a dental practitioner. After insertion of the intra-oral imager into the oral cavity, the dental practitioner may capture images of visible parts of the teeth and the gingivae. The 3D intra-oral imager may be fabricated in the form of a slender rod that is referred to as a wand or a handpiece. The wand may be approximately the size of a dental mirror with a handle that is used in dentistry. The wand may have a built-in light source and a video camera that may achieve an imaging magnification, ranging in scale from 1/10 to 40 times or more. This allows the dental practitioner to discover certain types of details and defects of the teeth and gums. The images captured by the intra-oral camera may be displayed on a display unit.

Certain types of feedback control mechanisms comprise a closed loop system that utilize information obtained from measuring output variables of the system to iteratively adjust input parameters that comprise the manipulated variables of the system. In feedback control mechanisms, an output variable of the system is measured and compared with a target value. This difference between the actual measured value and the desired target value is referred to as the tracking error in the measured output variable. Feedback control mechanisms may adjust the input parameters, i.e., the manipulated variables, of the system to minimize this tracking error in the measured output variable. There are many types of feedback control mechanisms, including proportional control, proportional-derivative control, proportional-integral control, proportional-integral-derivative control, etc.

SUMMARY OF THE PREFERRED EMBODIMENTS

Provided are a method, system, and computer readable storage medium in which data is received from a dental imaging system. The received data is analyzed to adjust one or more imaging parameters of the dental imaging system. In further embodiments, the received data corresponds to measured output variables of a feedback control mechanism. The one or more imaging parameters correspond to manipulated variables of the feedback control mechanism, where the one or more imaging parameters are adjusted iteratively in real-time via the feedback control mechanism by reducing tracking error between measured and targeted values of the received data.

In additional embodiments, the dental imaging system has an illumination source that illuminates one or more teeth at an illumination level, where the illumination level is adjusted, based on analyzing at least one of reflectivity and distribution of pixels corresponding to grayscales, in one or more images of the one or more teeth.

In yet additional embodiments, an exposure parameter of the dental imaging system is a function of an illumination level and an integration time. The integration time of the dental imaging system is adjusted based on analyzing one or more images of one or more teeth acquired by the dental imaging system.

In further embodiments, the dental imaging system acquires images at a frame rate that is adjusted based on analyzing movements during acquisition of the images.

In yet further embodiments, an adjustment is made to a frequency of a signal used for imaging one or more teeth in the dental imaging system, based on analyzing one or more images of the one or more teeth.

In certain embodiments, the dental imaging system has a mirror coupled to a heating element that controls temperature. The heating element of the mirror is adjusted based on measuring fogging in the dental imaging system.

In yet additional embodiments, an adjustment is made to an image cropping window, based on determining an area of interest in one or more images of one of more teeth acquired by the dental imaging system.

In additional embodiments, a gain of an imaging sensor of the dental imaging system is adjusted, based on determining whether one or more images of one of more teeth acquired by the dental imaging system lie within a dynamic range of the imaging sensor.

In further embodiments, adjustments are made to a spatial resolution of the dental imaging system, based a quality measure of one or more images of one of more teeth acquired by the dental imaging system.

Provided also is a control system for controlling a scanning wand, the control system comprising: a measurement component that measures an output variable, a manipulated variable adjustment component that adjusts one or more imaging parameters based on a tracking error between a measured value of the output variable and a targeted value of the output variable, and a tracking error adjustment component that determines the tracking error.

In certain embodiments, the manipulated variable adjustment component of the control system adjusts the one or more imaging parameters iteratively in real-time by reducing the tracking error between measured and targeted values of the output variable.

In further embodiments, the manipulated variable adjustment component of the control system adjusts an illumination level, based on analyzing at least one of reflectivity and distribution of pixels corresponding to grayscales, in one or more images of one or more teeth.

In further embodiments, the manipulated variable adjustment component of the control system adjusts an integration time based on analyzing one or more images of one or more teeth.

In yet further embodiments, the manipulated variable adjustment component of the control system adjusts a heating element of a mirror to raise or lower a temperature of the mirror, based on measurements of fogging.

Provided also is an imaging system, comprising an illumination source that illuminates one or more teeth at an illumination level, and an illumination source adjustment mechanism to adjust the illumination level, based on analyzing at least one of reflectivity and distribution of pixels corresponding to grayscales, in one or more images of one or more teeth.

Provided also is a dental imaging system comprising a mirror, and a heating element, where the heating element is adjusted to raise or lower a temperature of the mirror, based on a measurement of an extent of fogging.

Provided further is a dental imaging system comprising an illumination source that illuminates one or more teeth at an illumination level, and an integration time adjustment mechanism to adjust integration time, where an exposure parameter of the dental imaging system is a function of the illumination level and the integration time, and where the integration time of the dental imaging system is adjusted based on analyzing one or more images of one or more teeth acquired by the dental imaging system.

Provided also is a dental imaging system comprising an imaging sensor to acquire images at a frame rate, and a frame rate adjustment mechanism to adjust the frame rate, based on an analysis of movements during acquisition of the images by the imaging sensor.

In further embodiments, a dental imaging system comprises a signal generator that generates signal at a frequency, an imaging sensor to acquire one or more images of one or more teeth using the signal, and a signal frequency adjustment mechanism to adjust the frequency of the signal, based on analyzing the one or more images of the one or more teeth.

Provided further is a dental imaging system, comprising an imaging sensor to acquire one or more images of one or more teeth, and a gain adjustment mechanism to adjust a gain of the imaging sensor, based on determining whether the one or more images of one of more teeth acquired by the imaging sensor lie within a dynamic range of the imaging sensor.

BRIEF DESCRIPTION OF THE DRAWINGS

Referring now to the drawings in which like reference numbers represent corresponding parts throughout:

FIG. 5 illustrates a block diagram of a computing and imaging environment that includes a computational device that executes a feedback control application to control operations of an intra-oral imaging system, in accordance with certain embodiments;

DETAILED DESCRIPTION

In the following description, reference is made to the accompanying drawings which form a part hereof and which illustrate several embodiments. It is understood that other embodiments may be utilized and structural and operational changes may be made.

Certain embodiments provide a feedback control mechanism that adjusts imaging parameters in an intra-oral imaging system, by reducing or minimizing tracking error of measured output variables of the intra-oral imaging system. The tracking error is reduced or minimized by comparing target values of the measured output variables to the actual measured values.

Exemplary imaging parameters that are adjusted include the illumination level, the integration time, the exposure level, the frame rate, the frequency of signal, the temperature of a mirror, a cropping window, a camera gain, and a spatial resolution, etc. The exemplary output variables that are measured are based on the properties of acquired images, reflectivity, histogram of pixel grayscale values, motion during image acquisition, fogging levels, area of interest, translucency, image quality measures, etc.

Exemplary Embodiments

Figure 1:
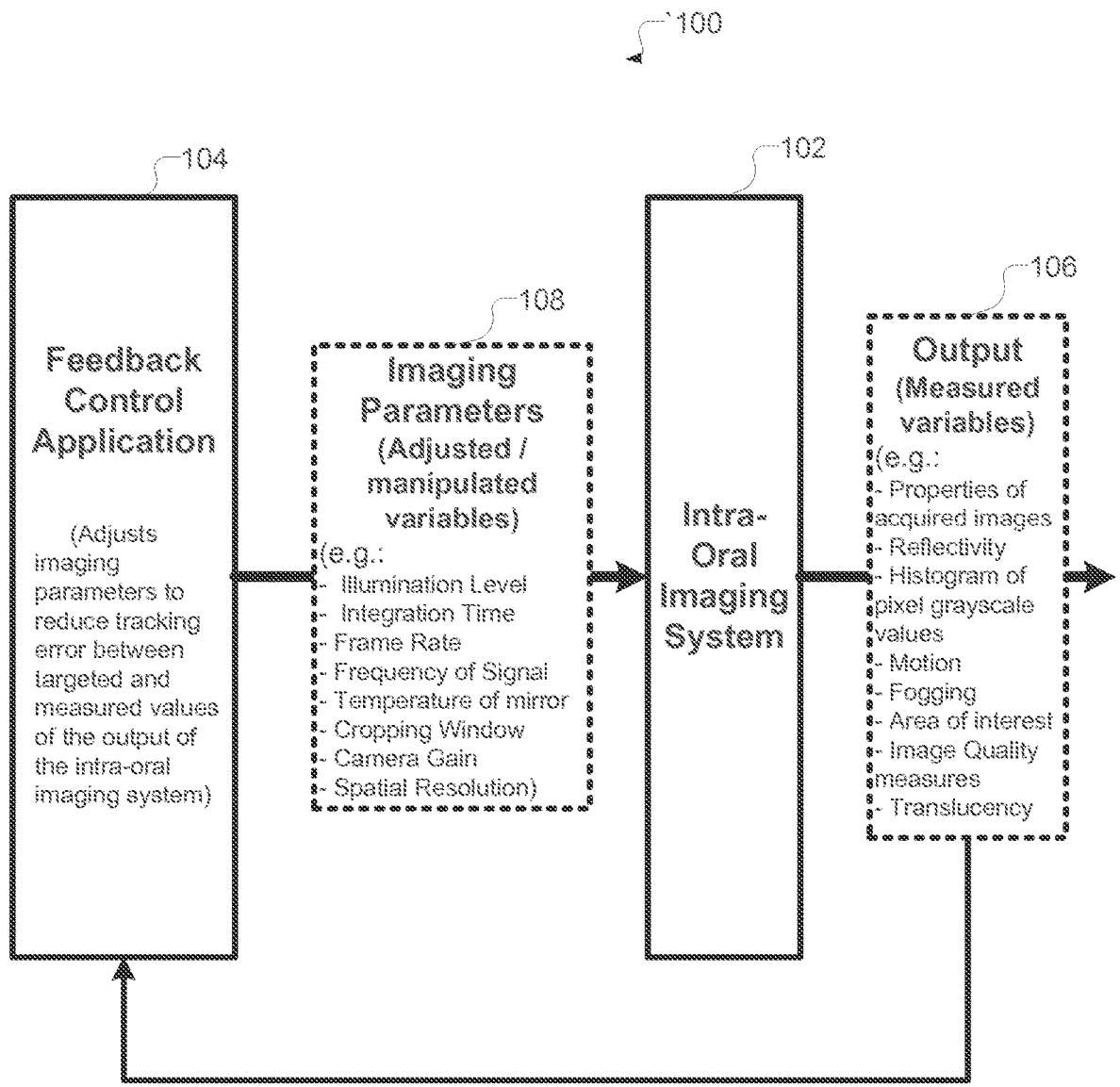
FIG. 1 illustrates a block diagram of a computing and imaging environment that includes an intra-oral imaging system coupled to a feedback control application, in accordance with certain embodiments.

FIG. 1 illustrates a block diagram of a computing and imaging environment 100 that includes an intra-oral imaging system 102 coupled to a feedback control application 104, in accordance with certain embodiments. The feedback control application 104 may be implemented in software, firmware, hardware or any combination thereof in certain embodiments, the feedback control application 104 may execute within the intra-oral imaging system 102, whereas in other embodiments the feedback control application 104 may execute in a computational device that is coupled to the intra-oral imaging system 102.

A dental practitioner may use die intra-oral imaging system 102 to acquire images of the dentition of a patient. The feedback control application 104 may analyze the output 106 of the intra-oral imaging system 102 and adjust imaging parameters 108 for acquiring images via the intra-oral imaging system 102. In feedback control system terminology, the output 106 of the intra-oral imaging system comprises measured variables, and the imaging parameters 108 comprise manipulated variables. Exemplary measured and manipulated variables are indicated via reference numerals 106, 108 in FIG. 1.

In certain embodiments, the feedback control application 104 adjusts the imaging parameters 108 to reduce tracking error between targeted and measured values of the output 106 of the intra-oral imaging system 102.

Figure 2:
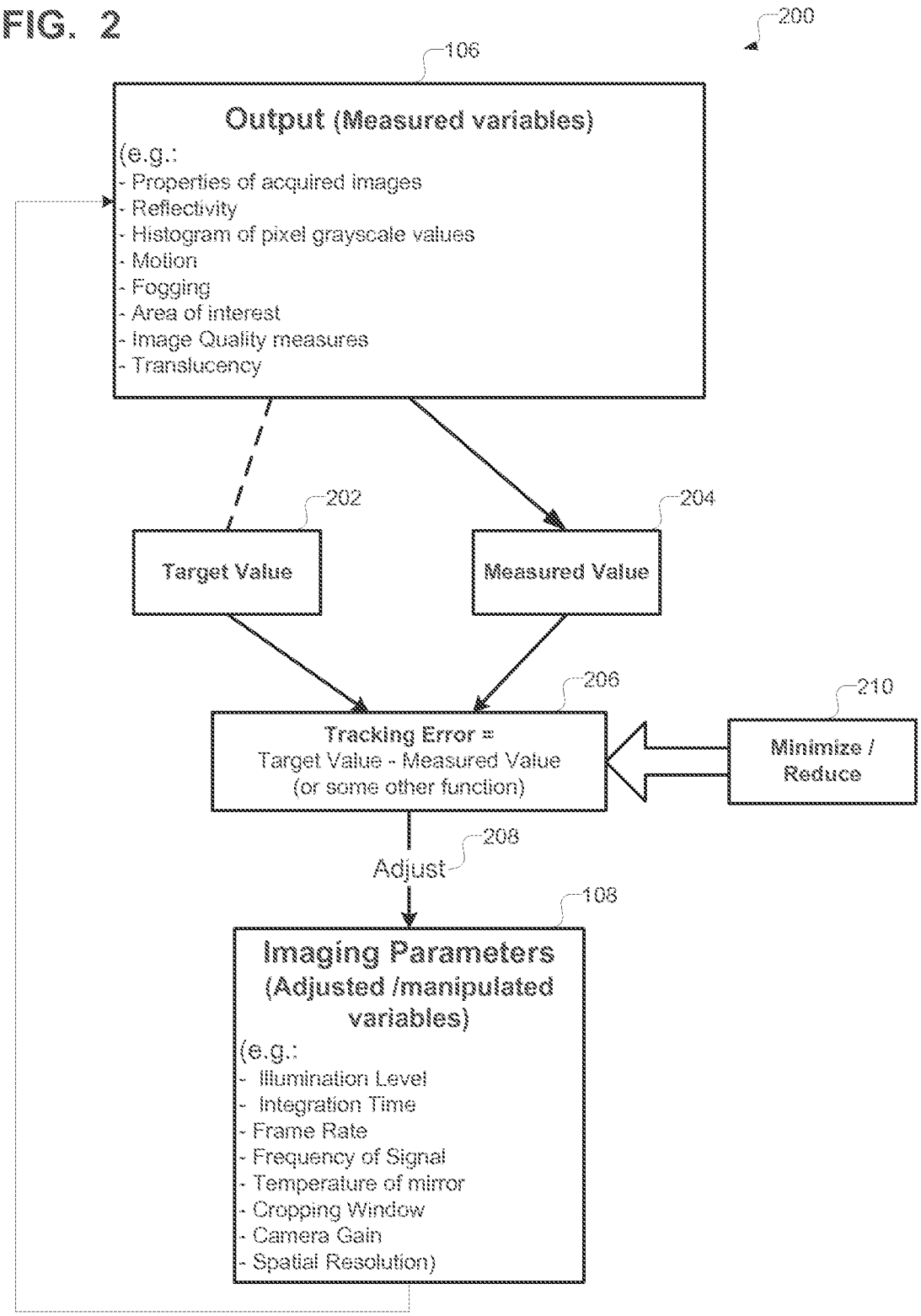
FIG. 2 illustrates a diagram that shows how adjustments are made to imaging parameters to reduce tracking error, in accordance with certain embodiments.

FIG. 2 illustrates a diagram 200 that shows how adjustments are made to imaging parameters 108 to reduce tracking error, in accordance with certain embodiments.

In certain embodiments, the output 106, i.e., the measured variables, of the intra-oral imaging system 102 may include properties of acquired images, reflectivity, histogram of pixel grayscale values, motion during image acquisition, fogging levels, area of interest, translucency, image quality measures, etc. Target values 202 of each of the measured variables may be defined by a dental practitioner, a system administrator, or a manufacturer of the intra-oral imaging system 102.

The feedback control application 104 determines the measured value 204 for each of the output variables. In certain embodiments, the measured values 204 and the target value 202 may each be tor a combination of variables instead of for a single variable.

The feedback control application 104 then determines a tracking error 206 by comparing the target value of the measured variable to the actual measured value. For example, in certain embodiments, the tracking error 206 may be the difference between the target value and the measured value. In other embodiments, the tracking error 206 may be the absolute value of the difference between the target value and the measured value. Other mechanisms may also be used to determine the tracking error 206.

The feedback control application 104 adjusts (shown via reference numeral 208) the imaging parameters 108 to minimize or reduce (shown via reference numeral 210) the tracking error 206. Exemplary imaging parameters that are adjusted include the illumination level, the integration time, the exposure level, the frame rate, the frequency of signal, the temperature of a mirror, a cropping window, a camera gain, and a spatial resolution, etc.

After the imaging parameters 108, i.e., the manipulated variables, have been adjusted, the output 106 of the intra-oral imaging system 102 is measured once again to secure measured values 204, and the tracking error 206 is computed once again to adjust the imaging parameters 108. The process continues till the tracking errors of the measured output variables have been minimized or reduced to a level less than a predetermined threshold.

Figure 3:
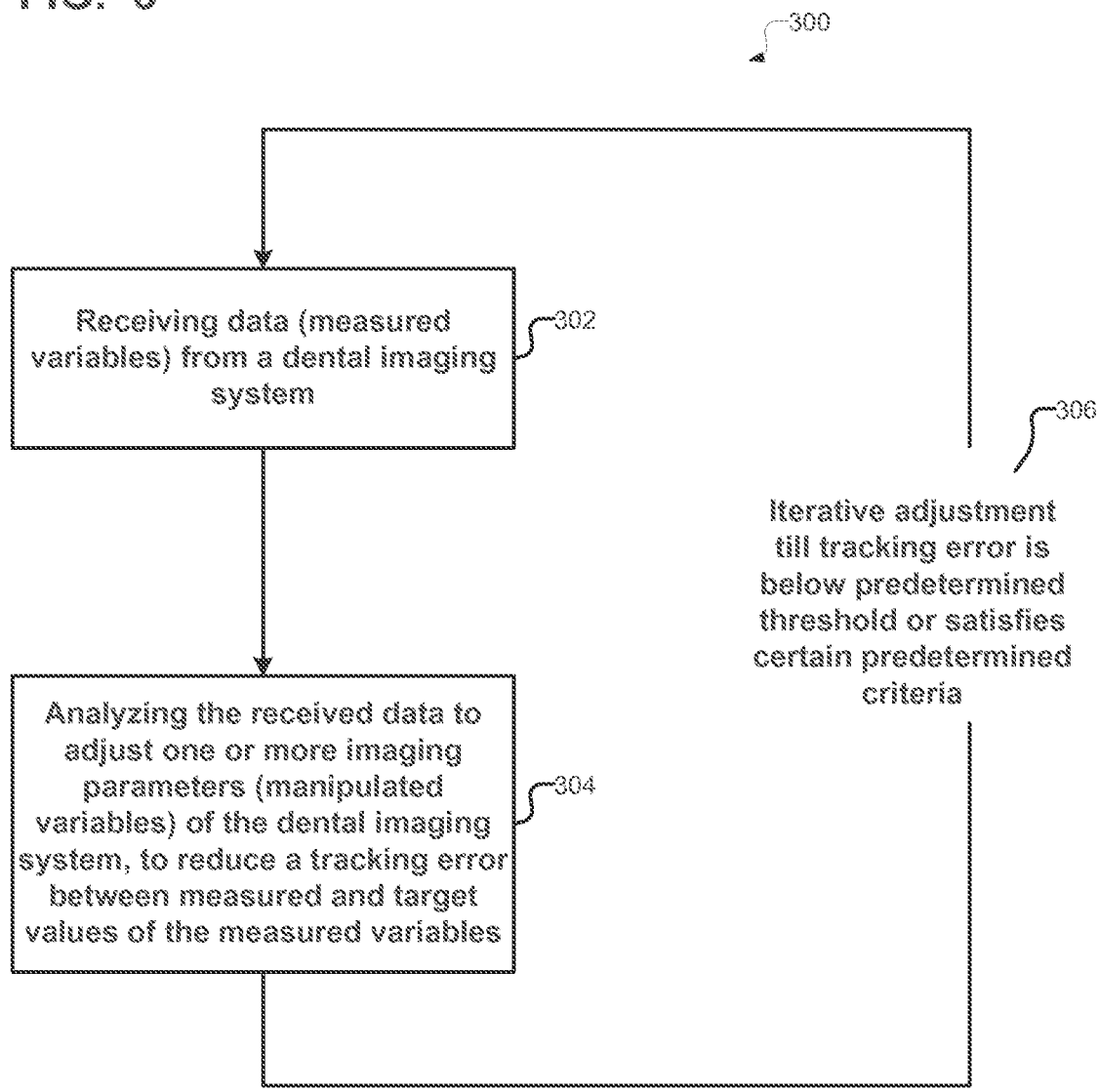
FIG. 3 illustrates a flowchart that shows operations performed by the feedback control application, in accordance with certain embodiments.

FIG. 3 illustrates a flowchart 300 that shows operations performed by the feedback control application 104, in accordance with certain embodiments. The operations shown in FIG. 3 may be performed by the feedback control application 104 that executes in the intra-oral imaging system 102 or in a computational device coupled to the intra-oral imaging system 102.

Control starts at block 302, in which the feedback control application 104 receives data (i.e., the output measured variables) from a dental imaging system, such as the intra-oral imaging system 102. Control proceeds to block 304 where the feedback control application 104 analyzes the received data to adjust one or more imaging parameters (i.e., manipulated variables) of the dental imaging system, to reduce a tracking error between measured and target values of the measured variables. Control then returns to block 302 (as shown via reference numeral 306) until the tracking error is below a predetermined threshold or satisfies certain predetermined criteria.

Figure 4:
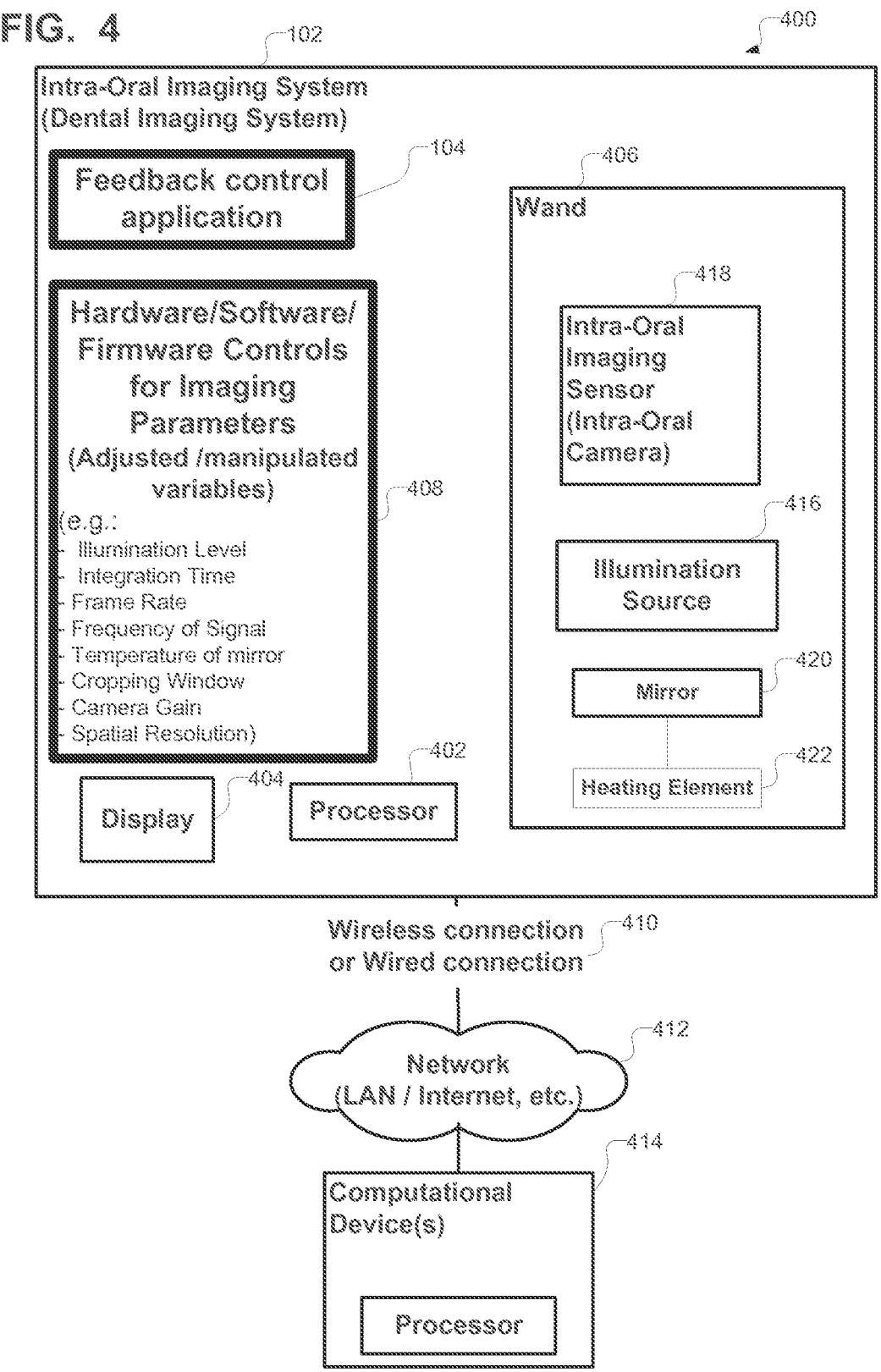
FIG. 4 illustrates a block diagram of a computing and imaging environment that includes an intra-oral imaging system that executes a feedback control application, in accordance with certain embodiments.

FIG. 4 illustrates a block diagram of a computing and imaging environment 400 that includes the intra-oral imaging system 102, where the intra-oral imaging system 102 executes the feedback control application 104, in accordance with certain embodiments.

The intra-oral imaging system 102 is comprised of a processor 402, a display unit 404, a wand 406, and the feedback control application 104. Controls 408 implemented in hardware, software, or firmware are provided in the intra-oral imaging system 102, for adjusting the imaging parameters 108.

In certain embodiments, the intra-oral imaging system 102 may be coupled via a wired or wireless connection 410 over a network 412 to one or more computational devices 414, where the computational devices may include any suitable computational device such as a personal computer, a server computer, a mini computer, a mainframe computer, a blade computer, a tablet computer, a touch screen computing device, a telephony device, a cell phone, a mobile computational device, etc., and some of the computational devices may provide web services or cloud computing services.

A dental practitioner may hold the wand 406 inside a patient's oral cavity. An optical illumination source 416 that is coupled to the wand 406 may illuminate the oral cavity, and an intra-oral imaging sensor 418 may be used to capture a plurality of digital images of structures in the oral cavity, such as the patient's teeth, gingivae, and/or palate, and other structures, such as fillings, braces, etc. In certain embodiments the intra-oral imaging sensor 418 may comprise an intra-oral camera. A mirror 420 coupled to a heating element 422 whose temperature is adjustable to heat the mirror 420 is also included as a part of the wand 406.

The operation of the wand 406 may be controlled by the feedback control application 104 that may be implemented in software, hardware, firmware or any combination thereof in certain embodiments, the display unit 404 of the intra-oral imaging system 102 may include a touch screen display unit. The feedback control application 104 may process the images acquired by the intra-oral imaging sensor 418 and display the images on the display unit 404 and optionally transmit the images to computational device 414.

Therefore, FIG. 4 illustrates certain embodiments in which a feedback control application 104 adjusts hardware, software, or firmware based controls 408 for imaging parameters that are included in an intra-oral imaging system 102 that comprises a dental imaging system.

FIG. 5 illustrates a block diagram of a computing and imaging environment 500 that includes a computational device 502 that executes the feedback control application 104 to control operations of an intra-oral imaging system 504, in accordance with certain embodiments. The intra-oral imaging system 504 is coupled to the computational device 502 via a wireless or wired connection 506 over a network 508. The intra-oral imaging system 504 includes a display unit 510, a processor 512, a wand 514, and hardware, software, or firmware based controls 516 for imaging parameters. Included in the wand 514 are an intra-oral imaging sensor 518, an illumination source 520, and a mirror 522 that is heated by a heating element 524.

In FIG. 5, the feedback control application 104 executes operations on the processor 526 of the computational device 502 to adjust imaging parameters for the intra-oral imaging system 504 by adjusting the hardware, software, or firmware based controls 516 for imaging parameters.

Figure 6:
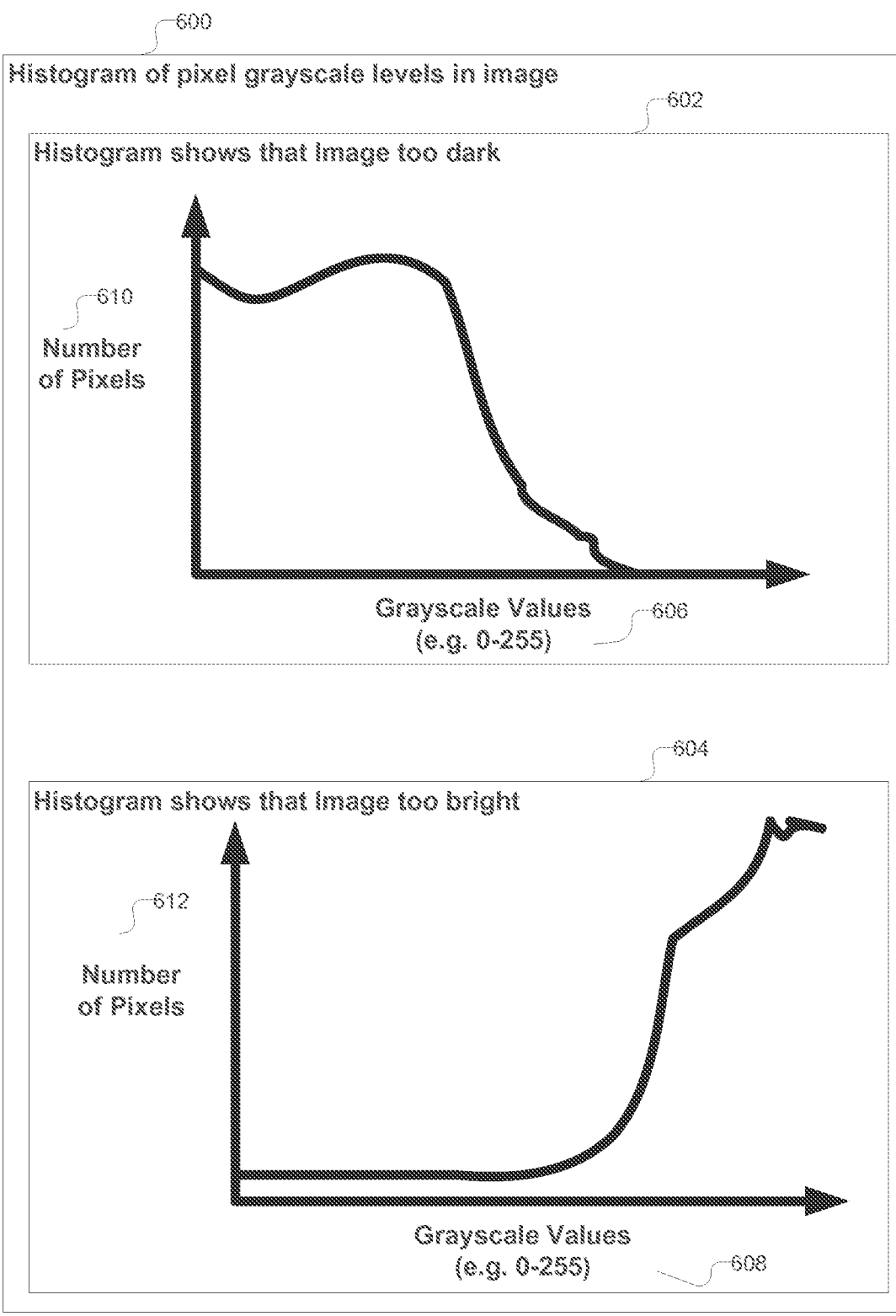
FIG. 6 illustrates block diagram that shows how to determine whether an image is too bright or too dark based on histograms of pixel grayscale levels in an image, in accordance with certain embodiments.

FIG. 6 illustrates block diagram 600 that snows how to determine whether an image is too bright or too dark based on histograms 602, 604 of pixel grayscale levels in an image, in accordance with certain embodiments.

In the histograms 602, 604 the horizontal axis shows the grayscale values 606, 608 of the acquired image. In certain embodiments, the grayscale values vary between 0 and 255. A grayscale value of 0 means that that the pixel is black and the grayscale value of 255 means that that pixel is white. The number of pixels 610, 612 are shown on the vertical axis.

From histogram 602 it can be observed that the image is likely to be rather dark as the overwhelming majority of pixels have grayscale values that are low, and in the histogram of 604 it can be observed that the image is likely to be too bright as the overwhelming majority of pixels have grayscale values that are high. In certain embodiments, the feedback control application 104 may analyze the histograms for one or more images, and then adjust imaging parameters 108 to produce better quality images that are neither too dark nor too bright. In certain embodiments, certain types of histogram equalization may also be facilitated by the adjustment of imaging parameters 108 via the feedback control application 104.

Figure 7:
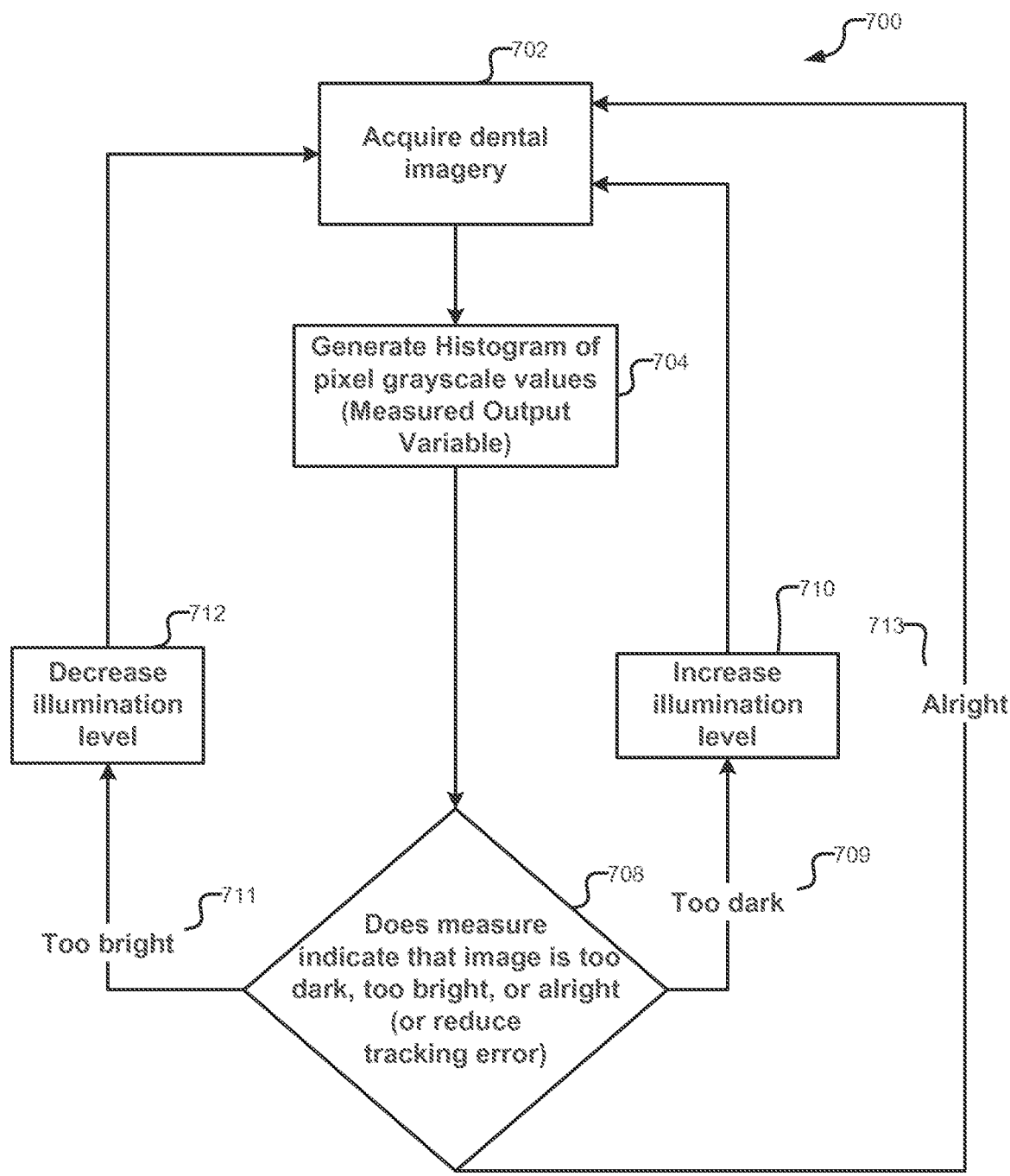
FIG. 7 illustrates a flowchart that shows how to adjust an illumination level in the intra-oral imaging system via the feedback control application, in accordance with certain embodiments.

FIG. 7 illustrates a flowchart 700 that shows how to adjust an illumination level in the intra-oral imaging system 102 via the feedback control application 104, in accordance with certain embodiments.

Control starts at block 702 in which the intra-oral imaging system 102 acquires dental imagery. The feedback control application 104 generates (at block 704) a histogram of pixel grayscale values, which comprise the measured output variable. A determination is made (at block 708) as to whether the measured output variable indicates that the image is too dark, too bright, or alright, based on a tracking error. If the image is too dark (shown via reference numeral 709), then the illumination level is increased (block 710). If the image is too bright (reference numeral 711) then the illumination level is decreased (block 712). If the image is alright (block 713), i.e., the tracking error is minimized, then the process continues to block 702 where more dental imagery is acquired. The target value for the output measured variable may be a value calculated from a histogram that is neither too dark nor too bright.

While FIGS. 6 and 7 have described embodiments that use grayscale values, in other embodiments color may be used to adjust the illumination level.

Figure 8:
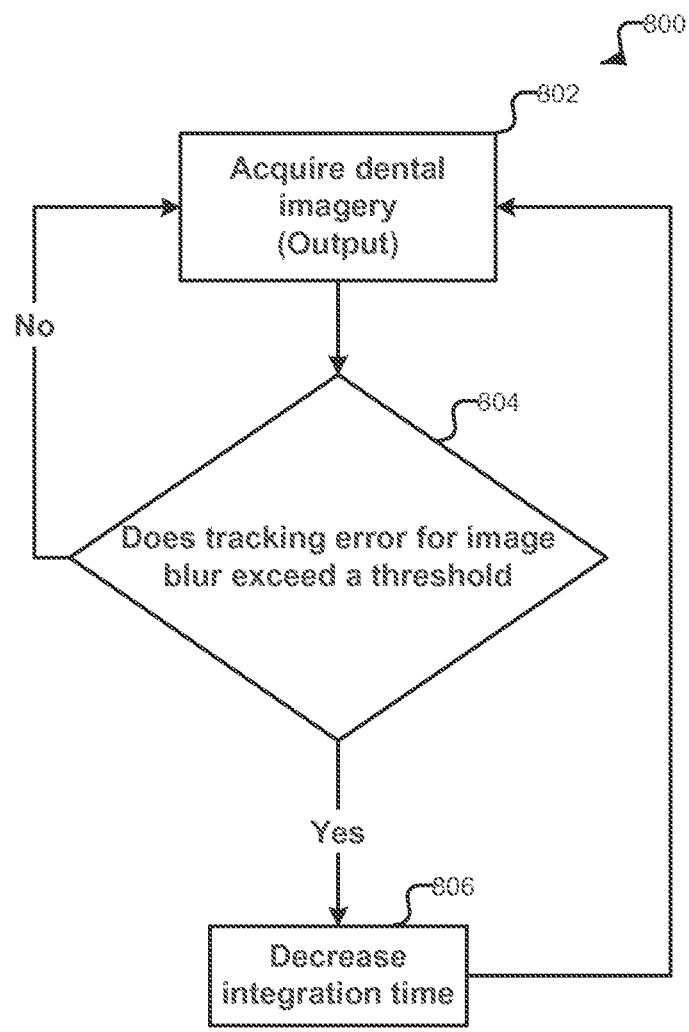
FIG. 8 illustrates a flowchart that shows how to adjust integration time in the intra-oral imaging system via the feedback control application, in accordance with certain embodiments.

FIG. 8 illustrates a flowchart 800 that shows how to adjust integration time in the intra-oral imaging system 102 via the feedback control application 104, in accordance with certain embodiments.

Control starts at block 802 in which dental imagery is acquired, and a determination is made at block 804 as to whether the tracking error for image blur exceeds a threshold. If so, then the integration time (i.e., the amount of time that a signal is used for imaging a frame) is decreased (at block 806) to reduce the amount of blur in the images and control returns to block 802. If not, then the process continues to block 802 where additional dental imagery is acquired.

Figure 9:
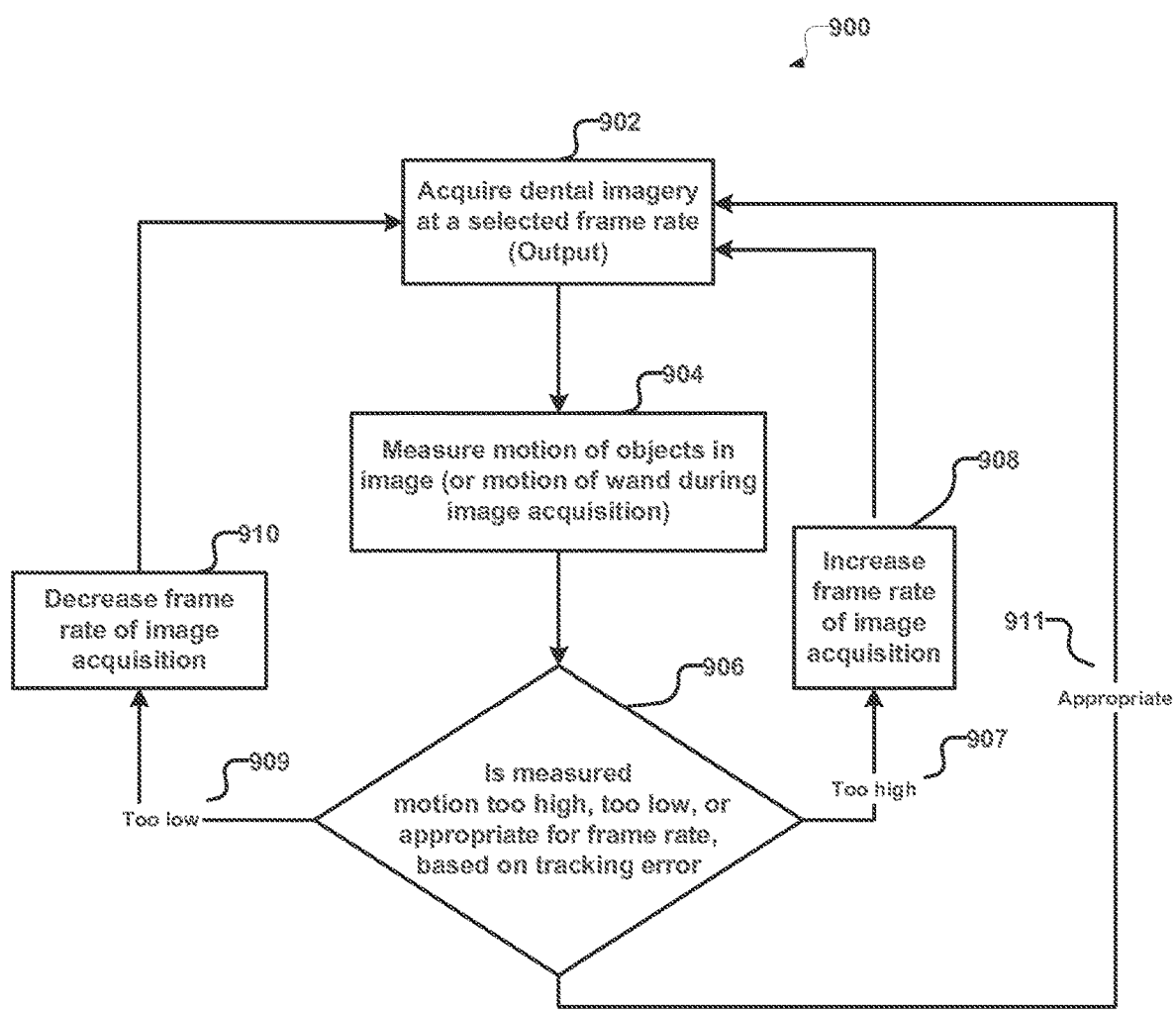
FIG. 9 illustrates a flowchart that shows how to adjust a frame rate in the intra-oral imaging system via the feedback control application, in accordance with certain embodiments.

FIG. 9 illustrates a flowchart 900 that shows how to adjust a frame rate in the intra-oral imaging system 102 via the feedback control application 104, in accordance with certain embodiments.

Control starts at block 902 in which dental imagery is acquired at a selected frame rate. The frame rate is the number of frames acquired per second. Control proceeds to block 904 in which motion of objects in dental imagery or motion of wand during image capture is determined. A determination is made (at block 906) based on the tracking error whether the measured motion is too high, too low, or appropriate, if the motion is too high (reference numeral 907), then the mime rate of image acquisition is increased (block 908). If measured motion is too low (reference numeral 909) then the frame rate of image acquisition is decreased (block 910). If the motion is appropriate (reference numeral 911), i.e., the tracking error has been minimized, then the process returns to block 902 where additional dental imagery is acquired without any change in the frame rate.

Figure 10:
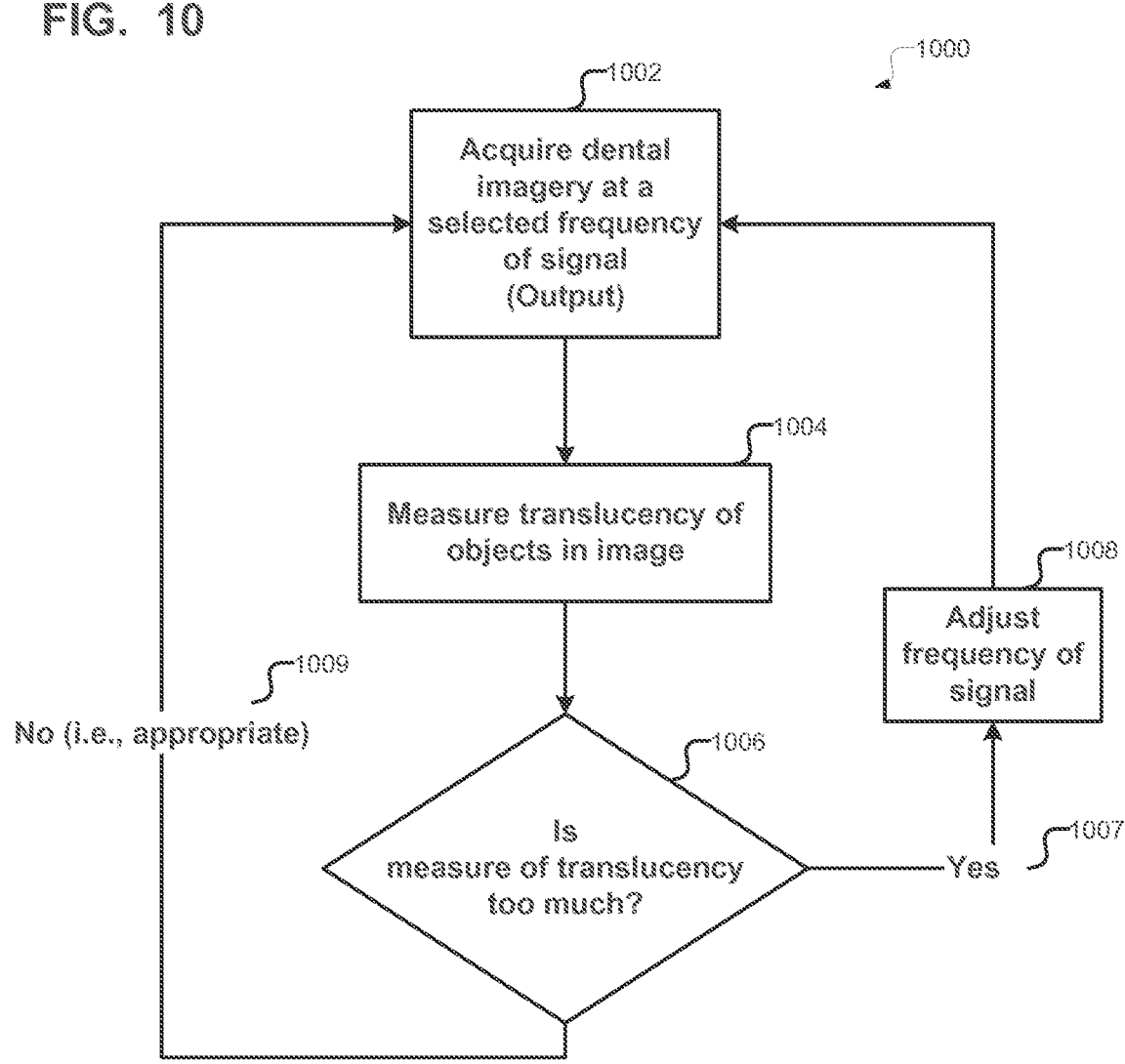
FIG. 10 illustrates a flowchart that shows how to adjust a frequency of signal in the intra-oral imaging system via the feedback control application, in accordance with certain embodiments.

FIG. 10 illustrates a flowchart 1000 that shows how to adjust a frequency of signal in the intra-oral imaging system 102 via the feedback control application 104, in accordance with certain embodiments.

Control starts at block 1002 in which dental imagery is acquired at a selected frequency for the illumination signal. For example, frequencies corresponding to 405 nm wavelengths may be used in certain embodiments. Translucency properties of objects in acquired images may be measured (at block 1004), and a determination may be made based on the tracking error as to whether the measure of translucency is too much (block 1006). If so ("Yes" branch 1007), then control proceeds to block 1008 where the frequency of the signal is adjusted to reduce the translucency and control returns to block 1002. If not ("No" branch 1009), then control returns to block 1002 to acquire additional dental imagery because the tracking error has been minimized. Multiple diodes may be used to change the frequency of the signal from one frequency to another, where one diode operates at one frequency and another diode operates at another frequency.

Figure 11:
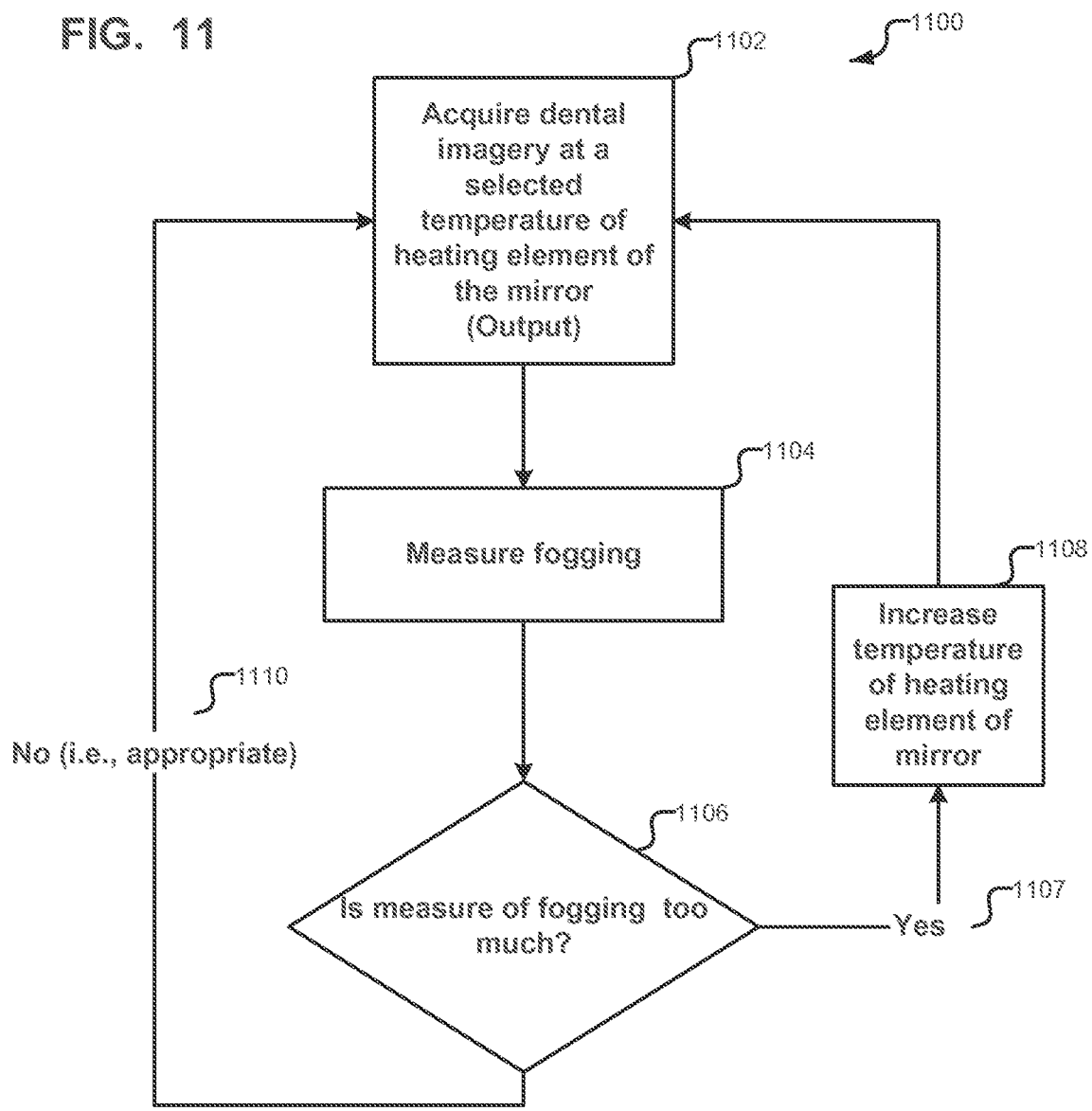
FIG. 11 illustrates a flowchart that shows how to adjust the temperature of a heating element coupled to a mirror of the intra-oral imaging system via the feedback control application, in accordance with certain embodiments.

FIG. 11 illustrates a flowchart 1100 that shows how to adjust the temperature of a heating element 422, 524 coupled to a mirror 420, 522 of the intra-oral imaging system 102, 504 via the feedback control application 104, in accordance with certain embodiments.

Control starts at block 1102, in which dental imagery is acquired at a selected temperature of the heating elements 422, 524 of the mirror 420, 522. Control proceeds to block 1104 where logging is measured. At block 1106, a determination is made as to whether the measure of fogging is too much based on the tracking error. If so (i.e., "yes" branch 1107), control proceeds to block 1108 where the temperature of the beating element 422, 524 of the mirror 420, 522 is increased, and control returns to block 1102. If not (i.e., "no" branch 1110), then control returns to block 1102 to acquire additional dental imagery.

Figure 12:
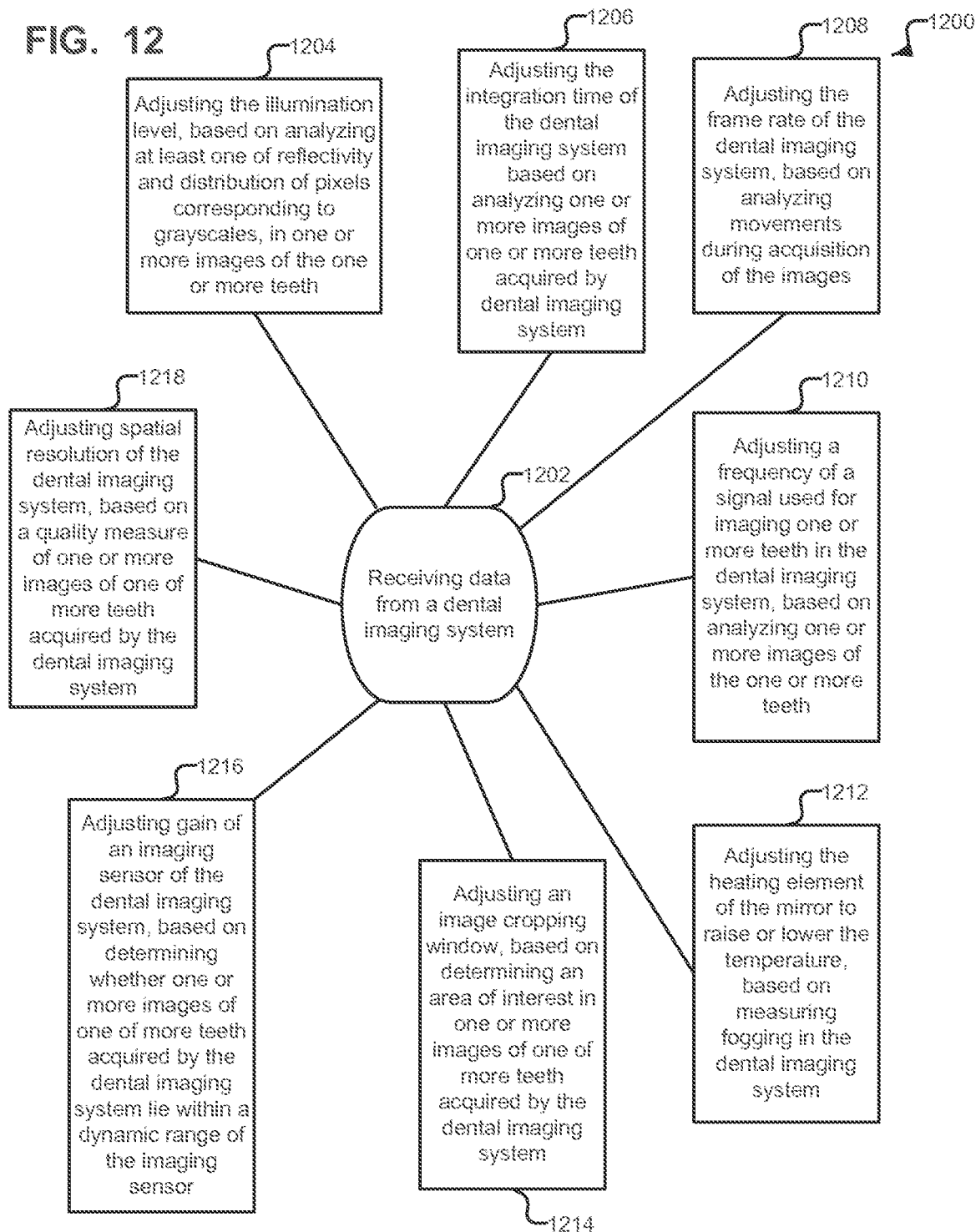
FIG. 12 illustrates a block diagram that shows operations performed in the ultra-oral imaging system via the feedback control application, in accordance with certain embodiments.

FIG. 12 illustrates a block diagram 1200 that shows operations performed in the intra-oral imaging system 102 via the feedback control application 104, in accordance with certain embodiments.

Control starts at block 1202 in which data is received from a dental imaging system, such as the intra-oral imaging system 102. Control may proceed from block 1202, either sequentially or in parallel, to blocks 1204, 1206, 1208, 1210, 1212, 1214, 1216, 1218.

In block 1204, the dental imaging system 102 has an illumination source 416 that illuminates one or more teeth at an illumination level, where the illumination level is adjusted, based on analyzing at least one of reflectivity and distribution of pixels corresponding to grayscales, in one or more images of the one or more teeth. In other embodiments, image modulation, signal to noise ratio, etc. may be used for adjusting the image illumination level when one or more images are being acquired for three-dimensional surface reconstruction. To provide an example, images of gold crowns may show a specular surface and illumination level may be adjusted to image the gold crowns in a suitable manner.

In block 1206, an exposure parameter of the dental imaging system 102 is a function of an illumination level and an integration time (e.g., a product of the illumination level and the integration time). The integration time of the dental imaging system 102 is adjusted based on analyzing one or more images of one or more teeth acquired by dental imaging system 102.

In block 1208, the dental imaging system 102 acquires images at a frame rate that is adjusted based on analyzing movements during acquisition of the images.

In block 1210, an adjustment is made to a frequency of a signal used for imaging one or more teeth in the dental imaging system 102, based on analyzing one or more images of the one or more teeth.

In block 1212, the dental imaging system 102 has a mirror 420 coupled to a heating element 422 that controls temperature. The heating element 422 of the mirror 420 is adjusted, based on measuring fogging in the dental imaging system 102.

In block 1214, an adjustment is made to an image cropping window, based on determining an area of interest in one or more images of one of more teeth acquired by the dental imaging system 102. The image cropping window may show what region of the image is of interest to a dental practitioner and may remove extraneous images of the tin of the wand that may be included in acquired images of dentition.

In block 1216, a gain of an imaging sensor of the dental imaging system 102 is adjusted, based on determining whether one or more images of one of more teeth acquired by the dental imaging system 102 lie within the recommended dynamic range of the imaging sensor, where the dynamic range describes the ratio between the maximum and minimum measurable light intensities.

In block 1218, adjustments are made to a spatial resolution of the dental imaging system 102, based a quality measure of one or more images of one of more teeth acquired by the dental imaging system 102. If images are to be processed at a high speed, then to conserve processing power, the spatial resolution may be decreased, whereas if images are to be processed at a low speed then the spatial resolution is increased.

Figure 13:
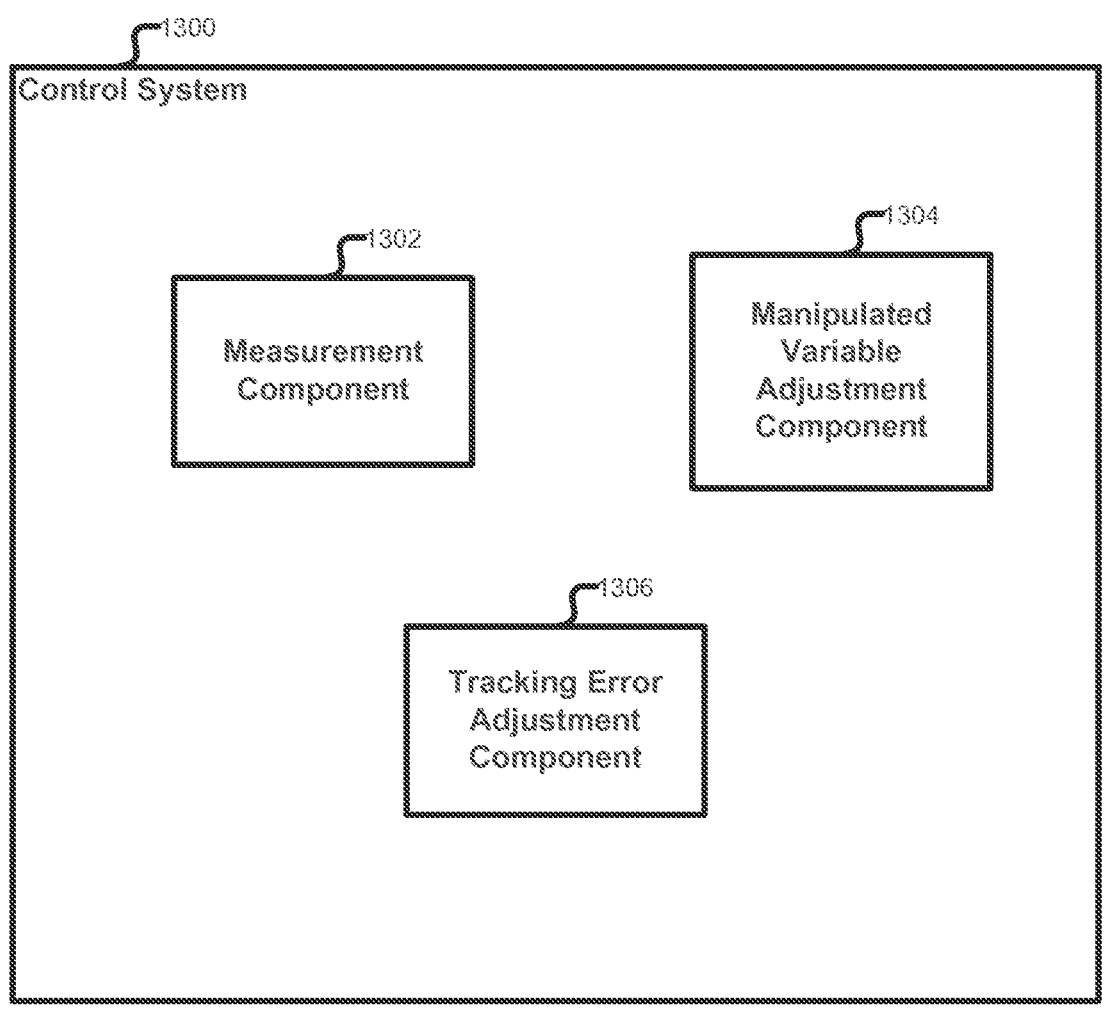
FIG. 13 shows components of a control system, in accordance with certain embodiments.

FIG. 13 shows components of a control system 1300 for controlling a scanning wand, such as wand 406, in accordance with certain embodiments. In certain embodiments the control system may be a hardware based control system. The control system 1300 comprises a measurement component 1302 that measures an output variable, a manipulated variable adjustment component 1304 that adjusts one or more imaging parameters based on a tracking error between a measured value of the output variable and a targeted value of the output variable, and a tracking error adjustment component 1306 that determines the tracking error.

In certain embodiments, the manipulated variable adjustment component 1304 of the control system 1300 adjusts the one or more imaging parameters iteratively in real-time by reducing the tracking error between measured and targeted values of the output variable. In further embodiments, the manipulated variable adjustment component 1304 of the control system 1300 adjusts an illumination level, based on analyzing at least one of reflectivity and distribution of pixels corresponding to grayscales, in one or more images of one or more teeth. In additional embodiments, the manipulated variable adjustment component 1304 of the control system 1300 adjusts an integration time based on analyzing one or more images of one or more teeth. In yet further embodiments, the manipulated variable adjustment component 1304 of the control system 1300 adjusts a heating element of a mirror to raise or lower a temperature of the mirror, based on measurements of fogging.

Figure 14:
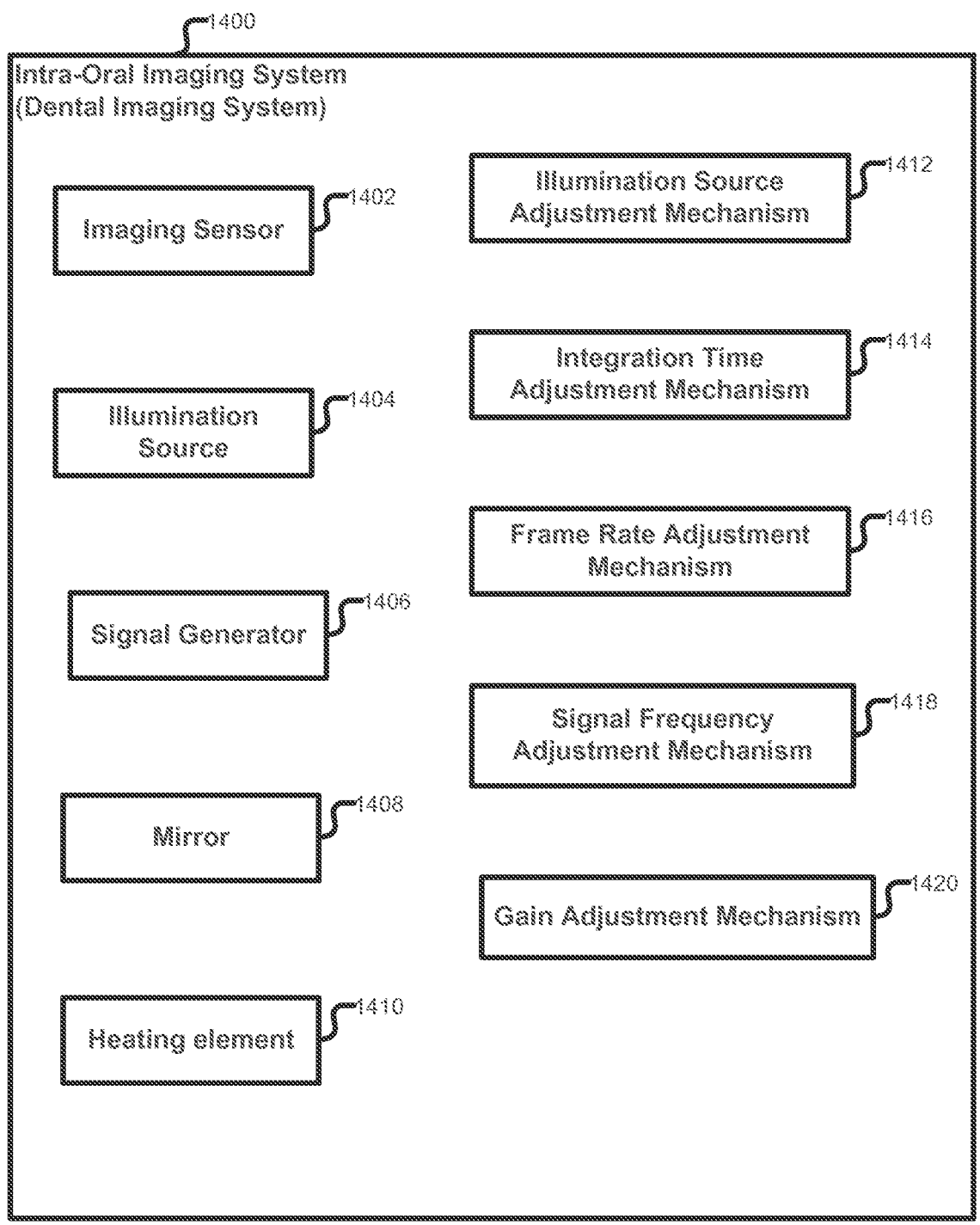
FIG. 14 shows components of a dental imaging system, in accordance with certain embodiments.

FIG. 14 shows components of a dental imaging system 1400 that may comprise an intra-oral imaging system, in accordance with certain embodiments.

In certain embodiments, the dental imaging system 1400 may comprise an illumination source 1404 that illuminates one or more teeth at an illumination level, and an illumination source adjustment mechanism 1412 to adjust the illumination level, based on analyzing at least one of reflectivity and distribution of pixels corresponding to grayscales, in one or more images of one or more teeth.

In certain embodiments the dental imaging system 1400 includes a mirror 1408, and a heating element 1410, where the heating element 1410 is adjusted to raise or lower a temperature of the mirror, based on a measurement of an extent of fogging.

In further embodiments the dental imaging system 1400 comprises an illumination source 1404 that illuminates one or more teeth at an illumination level, and an integration time adjustment mechanism 1414 to adjust integration time, where an exposure parameter of the dental imaging system 1400 is a function of the illumination level and the integration time, and where the integration time of the dental imaging system 1400 is adjusted based on analyzing one or more images of one or more teeth acquired by the dental imaging system 1400.

In certain embodiments, the dental imaging system 1400 comprises an imaging sensor 1402 to acquire images at a frame rate, and a frame rate adjustment mechanism 1416 to adjust the frame rate, based on an analysis of movements during acquisition of the images by the imaging sensor 1402.

In further embodiments, the dental imaging system 1400 comprises a signal generator 1406 that generates signal at a frequency, an imaging sensor 1402 to acquire one or more images of one or more teeth using the signal, and a signal frequency adjustment mechanism 1418 to adjust the frequency of the signal, based on analyzing the one or more images of the one or more teeth. The signal generator 1406 generates signals for the illumination source 1404 to illuminate the one or more teeth.

In additional embodiments, the dental imaging system 1400 comprises an imaging sensor 1402 to acquire one or more images of one or more teeth, and a gain adjustment mechanism 1420 to adjust a gain of the imaging sensor 1402, based on determining whether the one or more images of one of more teeth acquired by the imaging sensor 1402 lie within a dynamic range of the imaging sensor 1402.

Therefore, FIGS. 1-14 illustrate certain embodiments in which a feedback control application adjusts imaging parameters by minimizing tracking errors of measured outputs of an intra-oral imaging system, to improve the performance and quality measures of the intra-oral imaging system.

Additional Details of Embodiments

The operations described in the figures may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

A computer readable signal medium includes a propagated data signal with computer readable program code embodied therein. A computer readable signal medium may be any computer readable medium that is not a computer readable storage medium and that can communicate, propagate, or transport a program for use by or in connection with an instruction execution system, apparatus, or device. The computer readable storage medium is different from the computer readable signal medium.

Computer program code for carrying out operations for aspects of the present invention may be written in any combination of one or more programming languages.

Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 15:
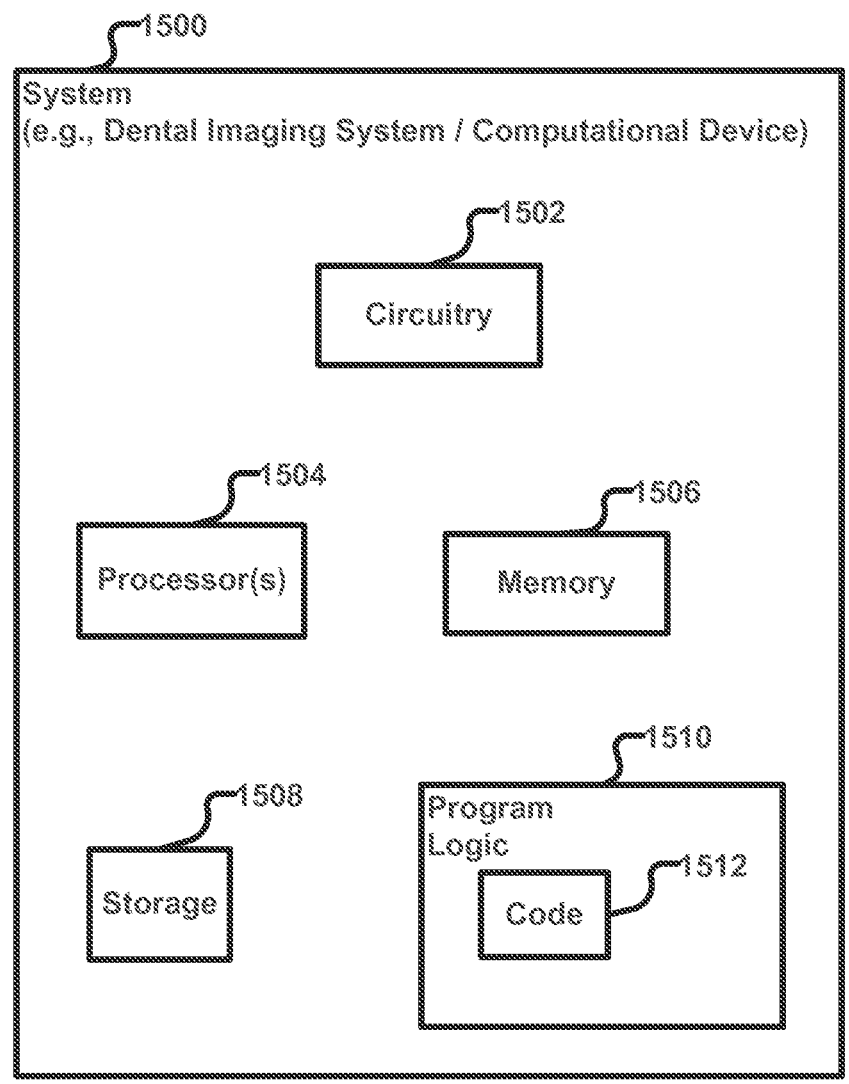
FIG. 15 illustrates a block diagram of a system that shows certain elements of the intra-oral imaging system or a computational device that executes a feedback control application, in accordance with certain embodiments.

FIG. 15 illustrates a block diagram that snows certain elements that may be included in a system 1500, where in the system 1500 may be the intra-oral imaging system 102, 504 or the computational device 414, 502 in accordance with certain embodiments. The system 1500 may include a circuitry 1502 that may in certain embodiments include at least a processor 1504. The processor 1504 may comprise any suitable processor known in the art, such as, an arithmetic logical unit, a central processing unit, a circuitry that performs operations, hardware that performs instructions of a computer program, a microprocessor, a parallel processor, an array processor, a vector processor, a transistorized central processing unit, a microcontroller, a logic circuitry, etc. Any device that manipulates digital information based on one or more operational instructions or in a predefined manner is an example of the processor 1504. The system 1500 may also include a memory 1506 (e.g., a volatile memory device), and storage 1508. The storage 1508 may include a non-volatile memory device (e.g., EEPROM, ROM, FROM, RAM, DRAM, SRAM, flash, firmware, programmable logic, etc.), magnetic disk drive, optical disk drive, tape drive, etc. The storage 1508 may comprise an internal storage device, an attached storage device and/or a network accessible storage device. The system 1500 may include a program logic 1510 including code 1512 that may be loaded into the memory 1506 and executed by the processor 1504 or circuitry 1502. In certain embodiments, the program logic 1510 including code 1512 may be stored in the storage 1508. In certain other embodiments, the program logic 1510 may be implemented in the circuitry 1502. Therefore, while FIG. 15 shows the program logic 1510 separately from the other elements, the program logic 1510 may be implemented in the memory 1506 and/or the circuitry 1502.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that ail such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method for using a dental imaging system, the method comprising:
   receiving image data from the dental imaging system;
   analyzing, via a processor, the received image data to measure one or more image properties;
   determining a tracking error by comparing the one or more measured image properties with a target value for each of the one or more image properties;
   while the tracking error is greater than a predetermined value,
   adjusting one or more imaging parameters corresponding to the one or more image properties to reduce the tracking error;
   receiving adjusted image data corresponding to the adjusted one or more imaging parameters from the dental imaging system;
   measuring one or more adjusted image properties of the adjusted image data; and
   iterating one or more times of at least determining the tracking error,
   wherein the one or more imaging parameters include an exposure parameter that is a function of an illumination level and an integration time, and wherein analyzing includes measuring an amount of image blur of the received image data,
   determining the tracking error includes comparing the measured image blur with a target amount of image blur, and
   adjusting includes adjusting the integration time to reduce the tracking error for image blur.

2. The method of claim 1, wherein the dental imaging system has an illumination source that illuminates one or more teeth and the one or more imaging parameters include an illumination level and wherein:
   analyzing the received image data includes generating a histogram of pixel grayscale values of the received image data;
   determining the tracking error includes determining image brightness based on the generated histogram; and
   adjusting one or more imaging parameters includes adjusting the illumination level based on the tracking error.

3. The method of claim 1, wherein the one or more imaging parameters include a frame rate, and wherein analyzing includes measuring motion in the received image data; and
   adjusting the frame rate based on the tracking error.

4. The method of claim 1, wherein the dental imaging system has an illumination source and the one or more imaging parameters include a selected frequency;
   analyzing includes measuring translucency properties of an object in the received image data at the selected frequency;
   determining the tracking error includes comparing the measured translucency with a predetermined threshold for translucency; and
   adjusting the selected frequency based on the tracking error.

5. The method of claim 1, wherein the dental imaging system has a mirror coupled to a heating element that controls temperature of the mirror, and wherein
   analyzing the received image data includes measuring an extent of fogging of the mirror; and
   adjusting includes increasing a temperature of the heating element based on the measured extent of fogging.

6. The method of claim 1, the method further comprising:
   adjusting an image cropping window, based on determining an area of interest in one or more images of one of more teeth acquired by the dental imaging system.

7. The method of claim 1, the method further comprising:
   adjusting gain of an imaging sensor of the dental imaging system, based on determining whether one or more images of one of more teeth acquired by the dental imaging system lie within a dynamic range of the imaging sensor.

8. The method of claim 1, the method further comprising:
   adjusting spatial resolution of the dental imaging system, based on a quality measure of one or more images of one or more teeth acquired by the dental imaging system.

9. A non-transitory computer readable storage medium for using a dental imaging system, wherein code stored in the non-transitory computer readable storage medium when executed by a processor causes operations, the operations comprising:
   receiving image data from the dental imaging system;
   analyzing the received image data to measure one or more image properties;
   determining a tracking error by comparing the one or more measured image properties with a target value for each of the one or more image properties;
   while the tracking error is greater than a predetermined value,
   adjusting one or more imaging parameters corresponding to the one or more image properties to reduce the tracking error; receiving adjusted image data corresponding to the adjusted one or more imaging parameters from the dental imaging system;
   measuring one or more adjusted image properties of the adjusted image data; and
   iterating one or more times of at least determining the tracking error,
   wherein the one or more imaging parameters include an exposure parameter that is a function of an illumination level and an integration time, and wherein analyzing includes measuring an amount of image blur of the received image data,
   determining the tracking error includes comparing the measured image blur with a target amount of image blur, and
   adjusting includes adjusting the integration time to reduce the tracking error for image blur.

10. The non-transitory computer readable storage medium of claim 9, wherein the dental imaging system has an illumination source that illuminates one or more teeth at an illumination level, the operations further comprising:
    adjusting the illumination level, based on analyzing at least one of reflectivity and distribution of pixels corresponding to grayscales, in one or more images of the one or more teeth.

11. The non-transitory computer readable storage medium of claim 9, wherein the dental imaging system has a mirror coupled to a heating element that controls a temperature of the mirror, and wherein analyzing the received image data includes measuring an extent of fogging of the mirror; and adjusting includes increasing a temperature of the heating element to raise the temperature of the mirror, based on the measured extent of fogging.

12. A control system for controlling a scanning wand, the control system comprising:
a measurement component that measures an output variable;
a manipulated variable adjustment component that adjusts one or more imaging parameters based on a tracking error between a measured value of the output variable and a targeted value of the output variable;
a processor; and
the non-transitory computer readable storage medium of claim 9 for determining the tracking error.

13. The control system of claim 12, wherein:
the manipulated variable adjustment component adjusts the one or more imaging parameters iteratively in real-time to reduce the tracking error between measured and targeted values of the output variable.

14. The control system of claim 12, wherein:
the manipulated variable adjustment component adjusts an illumination level, based on analyzing at least one of reflectivity and distribution of pixels corresponding to grayscales, in one or more images of one or more teeth.

15. The control system of claim 12, wherein:
the manipulated variable adjustment component adjusts an integration time based on analyzing one or more images of one or more teeth.

16. The control system of claim 12, wherein:
the manipulated variable adjustment component adjusts a heating element of a mirror to raise or lower a temperature of the mirror, based on measurements of fogging.

17. A dental imaging system, comprising:
an illumination source that illuminates one or more teeth at an illumination level;
the control system of claim 12; and
an illumination source adjustment mechanism to adjust the illumination level, based on the non-transitory computer readable storage medium analysis of at least one of reflectivity and distribution of pixels corresponding to grayscales, in the received image data.

18. A dental imaging system, comprising:
a mirror;
the control system of claim 12; and
a heating element, wherein the heating element is adjusted to raise or lower a temperature of the mirror, based on the non-transitory computer readable storage medium analysis of a measurement of an extent of fogging.

19. A dental imaging system, comprising:
an illumination source that illuminates one or more teeth at an illumination level;
a control system for controlling a scanning wand and including:
  a measurement component that measures an output variable;
  a manipulated variable adjustment component that adjusts one or more imaging parameters based on a tracking error between a measured value of the output variable and a targeted value of the output variable;
  a processor; and
  a non-transitory computer readable storage medium for using a dental imaging system, wherein code stored in the non-transitory computer readable storage medium when executed by the processor causes operations, the operations comprising:
    receiving image data from the dental imaging system;
    analyzing the received image data to measure one or more image properties;
    determining the tracking error by comparing the one or more measured image properties with a target value for each of the one or more image properties;
    while the tracking error is greater than a predetermined value,
    adjusting one or more imaging parameters corresponding to the one or more image properties to reduce the tracking error;
    receiving adjusted image data corresponding to the adjusted one or more imaging parameters from the dental imaging system;
    measuring one or more adjusted image properties of the adjusted image data; and
    iterating one or more times of at least determining the tracking error; and
an integration time adjustment mechanism to adjust integration time, wherein an exposure parameter of the dental imaging system is a function of the illumination level and the integration time, and wherein the integration time of the dental imaging system is adjusted based on the non-transitory computer readable storage medium analysis of one or more images of one or more teeth acquired by the dental imaging system.

20. A dental imaging system, comprising:
an imaging sensor to acquire images at a frame rate;
the control system of claim 12; and
a frame rate adjustment mechanism to adjust the frame rate, based on the non-transitory computer readable storage medium analysis of movements during acquisition of the images by the imaging sensor.

21. A dental imaging system, comprising;
a signal generator that generates signal at a frequency;
an imaging sensor to acquire one or more images of one or more teeth using the signal;
the control system of claim 12; and
a signal frequency adjustment mechanism to adjust the frequency of the signal, based on the non-transitory computer readable storage medium analysis of the one or more images of the one or more teeth.

22. A dental imaging system, comprising;
an imaging sensor to acquire one or more images of one or more teeth;
the control system of claim 12; and
a gain adjustment mechanism to adjust a gain of the imaging sensor, based on the non-transitory computer readable storage medium analysis of whether the one or more images of one or more teeth acquired by the imaging sensor lie within a dynamic range of the imaging sensor.

* * * * *